United States Patent
Hanson

(10) Patent No.: US 10,245,148 B2
(45) Date of Patent: Apr. 2, 2019

(54) FLEXIBLE SNAP-FIT PROSTHETIC COMPONENT

(71) Applicant: Howmedica Osteonics Corp., Mahwah, NJ (US)

(72) Inventor: Keenan Hanson, Sloatsburg, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 15/137,601

(22) Filed: Apr. 25, 2016

(65) Prior Publication Data

US 2017/0304059 A1    Oct. 26, 2017

(51) Int. Cl.
| | | |
|---|---|---|
| A61F 2/38 | (2006.01) |
| A61F 2/30 | (2006.01) |
| A61F 2/32 | (2006.01) |
| A61F 2/36 | (2006.01) |

(52) U.S. Cl.
CPC ............ *A61F 2/30767* (2013.01); *A61F 2/32* (2013.01); *A61F 2/36* (2013.01); *A61F 2/38* (2013.01); *A61F 2/3859* (2013.01); *A61F 2230/0093* (2013.01)

(58) Field of Classification Search
CPC ....... A61F 2/38; A61F 2/30767; A61F 2/3859
See application file for complete search history.

(56) References Cited

U.S. PATENT DOCUMENTS

| | | | |
|---|---|---|---|
| 4,355,429 A | 10/1982 | Mittelmeier et al. |
| 4,778,473 A | 10/1988 | Matthews et al. |
| 6,364,910 B1 | 4/2002 | Shultz et al. |
| 7,115,131 B2 | 10/2006 | Engh et al. |
| 7,520,901 B2 | 4/2009 | Engh et al. |
| 7,572,295 B2 | 8/2009 | Steinberg |
| 7,896,922 B2 | 3/2011 | Engh et al. |
| 8,398,715 B2 * | 3/2013 | Otto ...................... A61F 2/3886 623/20.14 |
| 8,545,569 B2 | 10/2013 | Fitz et al. |
| 8,690,945 B2 | 4/2014 | Fitz et al. |
| 8,814,946 B2 | 8/2014 | Steinberg |

(Continued)

OTHER PUBLICATIONS

Extended European Search Report for Appl. EP17167379.1 dated Jul. 4, 2017.

*Primary Examiner* — Dinah Baria
(74) *Attorney, Agent, or Firm* — Lerner, David, Littenberg, Krumholz & Mentlik, LLP

(57) ABSTRACT

Disclosed herein are flexible prosthetic components that are designed to be snap-fit to bone of a patient. The prosthetic components each have an outer articular surface and an inner bone contacting surface opposing the outer articular surface. The bone contacting surface has an anterior surface and an opposing posterior surface configured to contact corresponding anterior and posterior surfaces of the patient's bone. At least one of the anterior and posterior surfaces includes one or more protrusions extending outwardly therefrom. The anterior and posterior surfaces of the prosthetic components may flex toward and away from one another such that the one or more protrusions may snap-fit into corresponding recesses in the bone. The bone of the patient may be resected to include planar surfaces or resurfaced to include a curved surface corresponding to the respective bone contacting surface of the prosthetic components.

9 Claims, 11 Drawing Sheets

(56) References Cited

U.S. PATENT DOCUMENTS

| | | |
|---|---|---|
| 8,828,081 B2 | 9/2014 | Boyden et al. |
| 8,845,739 B2 | 9/2014 | Boyden et al. |
| 8,845,740 B2 | 9/2014 | Boyden et al. |
| 8,882,847 B2 | 11/2014 | Burdulis, Jr. et al. |
| 8,945,230 B2 | 2/2015 | Lang et al. |
| 8,979,938 B2 | 3/2015 | Linares |
| 9,089,434 B2 | 7/2015 | Ell |
| 9,114,012 B2 | 8/2015 | Wogoman |
| 9,162,008 B2 | 10/2015 | Serafin, Jr. et al. |
| 9,180,015 B2 | 11/2015 | Fitz et al. |
| 9,186,254 B2 | 11/2015 | Fitz et al. |
| 2007/0100462 A1 | 5/2007 | Lang et al. |
| 2007/0173858 A1 | 7/2007 | Engh et al. |
| 2007/0233141 A1* | 10/2007 | Park ............... A61B 17/155 606/88 |
| 2010/0312348 A1 | 12/2010 | Wang et al. |
| 2012/0330429 A1 | 12/2012 | Axelson, Jr. et al. |
| 2013/0144398 A1* | 6/2013 | Wogoman ......... A61F 2/3859 623/20.35 |
| 2014/0296929 A1 | 10/2014 | Stacey |
| 2014/0316526 A1 | 10/2014 | Grotz |

* cited by examiner

FLEXIBLE SNAP-FIT PROSTHETIC COMPONENT

FIELD OF THE INVENTION

The present invention relates to prosthetic components and surgical methods for artificial joint replacement, and in particular relates to flexible prosthetic components that can be snap-fit onto resected bone.

BACKGROUND OF THE INVENTION

Joint replacement surgery to remove and replace arthritic or dysfunctional joint surfaces with orthopedic prosthesis is widespread today. Hip and knee replacement operations are among the most commonly performed operations in the U.S. Knee replacement surgery can involve one or more damaged knee surfaces. Total knee arthroplasty ("TKA") is used to treat various forms of knee arthropathies, and is performed by removing and replacing all damaged articulating surfaces of the knee with a prosthetic component. Generally, TKA includes one or more of the following steps: a) removal of damaged cartilage along with a small amount of bone from the tibia and femur, b) replacement of damaged bone surfaces with metal components, and replacement of cartilage with medical grade plastic, c) resurfacing of the underside of the patella with a plastic disk, and d) inserting a piece of smooth, medical grade plastic between the metal parts to facilitate ease of movement.

Many different types of articulating material combinations are used to make prosthetic components. One of the more commonly used combinations includes a metal femoral surface articulating against a polymer tibia and patella surface. After implantation, the friction these components are subjected to may lead to metal erosion. Metal ions and debris released at the area of the implant can lead to complications such as osteolysis. Build-up of metal debris in soft body tissue can cause metallosis. Although poisoning from metallosis is rare, metal-on-metal implants containing cobalt-chromium alloys are known to cause arthroprosthetic cobaltism, which is an established health condition.

Stress shielding by stiff metal prosthetic implants can lead to bone resorption. Stress shielding is a mechanical phenomenon that occurs in prosthetic composites of stiff and flexible materials. In its natural state, a femur carries load by itself. However, when provided with a stiff metal implant, the femur is subject to reduced stress, hence stress shielded. Clinical patient series and animal experiments have shown that reduce stress loading can lead to bone loss. Changes in bone morphology have been linked to the effect of stress shielding and a subsequent adaptive remodeling process.

Stiff metal prosthesis are generally implanted to bone by long anchor pins and secured by using bone cement such as polymethylmethacrylate compositions, for example. Aseptic loosening of the bone cement surface, i.e., failure of the bond between an implant and bone in the absence of infection, has been observed in many cases.

BRIEF SUMMARY OF THE INVENTION

The present invention is for novel flexible prosthetic components and methods of securing these flexible prosthetic components to resected bone. The flexible prosthetic components disclosed herein have an outer articular surface and a bone contacting surface with one or more protrusions extending outwardly. The elasticity of the flexible prosthetic components in conjunction with fabricated protrusions will enable these prosthetic components to be slipped over and snap-fit around resected bone.

"Snap-fit" as used herein is a fixation method, whereby the elasticity of the flexible prosthetic is used to securely anchor prosthetic on resected bone by interlocking protrusions with corresponding recesses in resected bone. The flexible prosthetic components, which are smaller in their neutral state than the recipient bone, can be elastically deformed by the application of an external force by hand or special equipment to position the protrusions to align with corresponding recesses made in resected bone. Immediately upon removal of this external force, the deformed prosthetic will wrap around resected bone forcing protrusions to mate with recesses. Compressive forces of the flexible prosthetic acting on resected bone and stress induced by the interlocking fit between protrusions and recesses will result in secure mechanical retention.

Snap-fitting flexible prosthetic components on resected bone will simplify joint replacement surgery by eliminating or substantially reducing the need for bone cement. Interlocking components, i.e., protrusions and recesses, will facilitate in precise positioning of prosthetic on bone. Biocompatible flexible polymers used in making flexible prosthetic components will reduce or eliminate complications induced by commonly used metallic prosthetic components such as the release of metal ions and metallosis. Flexible polymers are inherently more flexible than their metal counterparts and will allow for natural loading on replaced joints. This will reduce bone stress shielding and consequently lead to less bone resorption.

A first aspect of the present invention is a flexible prosthetic component comprising of an outer annular surface, opposing bone contacting surfaces with one or more protrusions and recesses.

In one embodiment according to this first aspect of the present invention, the opposing bone contacting surfaces are parallel to each other and perpendicular to a distal surface. The sagittal distance between the opposing bone contacting surfaces is less than the corresponding bone dimension. The anterior and posterior bone contacting surfaces have multiple protrusions extending outward and parallel to the distal surface. Protrusions are fabricated to mate with corresponding recesses cut in resected bone.

In another embodiment according to the first aspect of this invention, the proximal ends of the opposing bone contacting surfaces are angled inwards and set at acute angles to a distal surface. The sagittal distance between the proximal ends of the opposing bone contacting surfaces is less than the corresponding bone dimension. The anterior and posterior bone contacting surfaces have multiple protrusions extending outward and parallel to the distal surface. Protrusions are fabricated to mate with corresponding recesses cut in resected bone.

In yet another embodiment of this first aspect, the opposing bone contacting surfaces are parallel to each other and perpendicular to a distal surface. The sagittal distance between the opposing bone contacting surfaces is less than the corresponding bone dimension. The anterior and posterior bone contacting surfaces have multiple protrusions extending outwardly and inferiorly towards a longitudinal axis. Protrusions are fabricated to mate with corresponding recesses cut in resected bone. The angled protrusions will ratchet into corresponding recesses in this embodiment and strengthen the interlocking of flexible prosthetic to resected bone.

In still yet another embodiment of this first aspect, an anterior bone contacting surface is obtusely angled to a distal surface and a posterior bone contacting surface is perpendicular to the distal surface. All interior bone contacting surfaces have multiple protrusions and recesses to mate with corresponding features in resected bone.

In still yet another embodiment of this first aspect, the bone contacting surface is a curved articular surface. The flexible prosthetic component in this embodiment is of substantially uniform thickness to snap-fit over a resurfaced distal femoral.

A second aspect of the present invention is a method for securing a flexible prosthesis component having an articular surface and an opposing surface to resected bone. The method comprises the steps of preparing protrusions and recesses in resected bone that correspond to protrusions and recesses in flexible prosthetic, inserting the protrusions at least partially into recesses, and applying force to the articular surface to deform flexible prosthetic to snap-fit the protrusions into recesses around resected bone upon release of external force.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
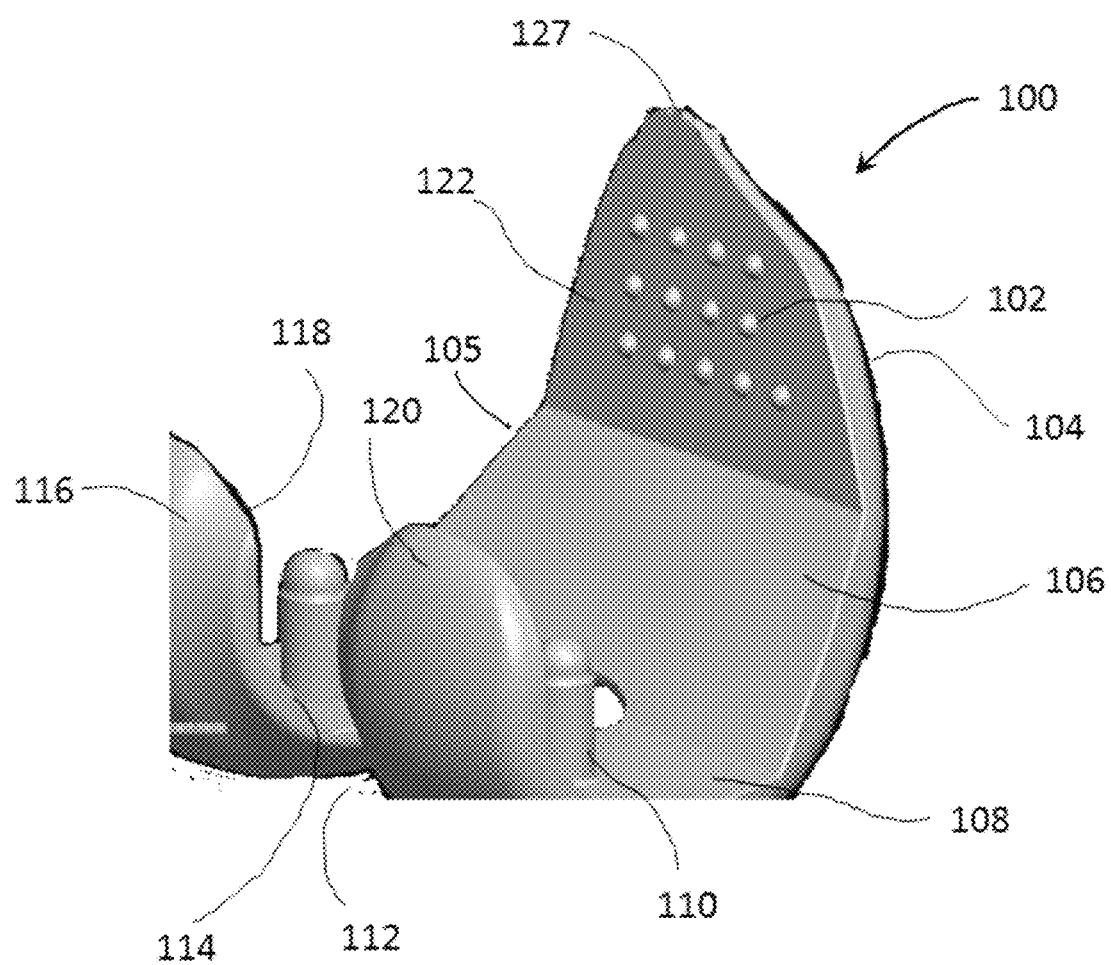
FIG. 1 is a perspective view of one embodiment of a flexible prosthetic component of the present invention.
Figure 2:
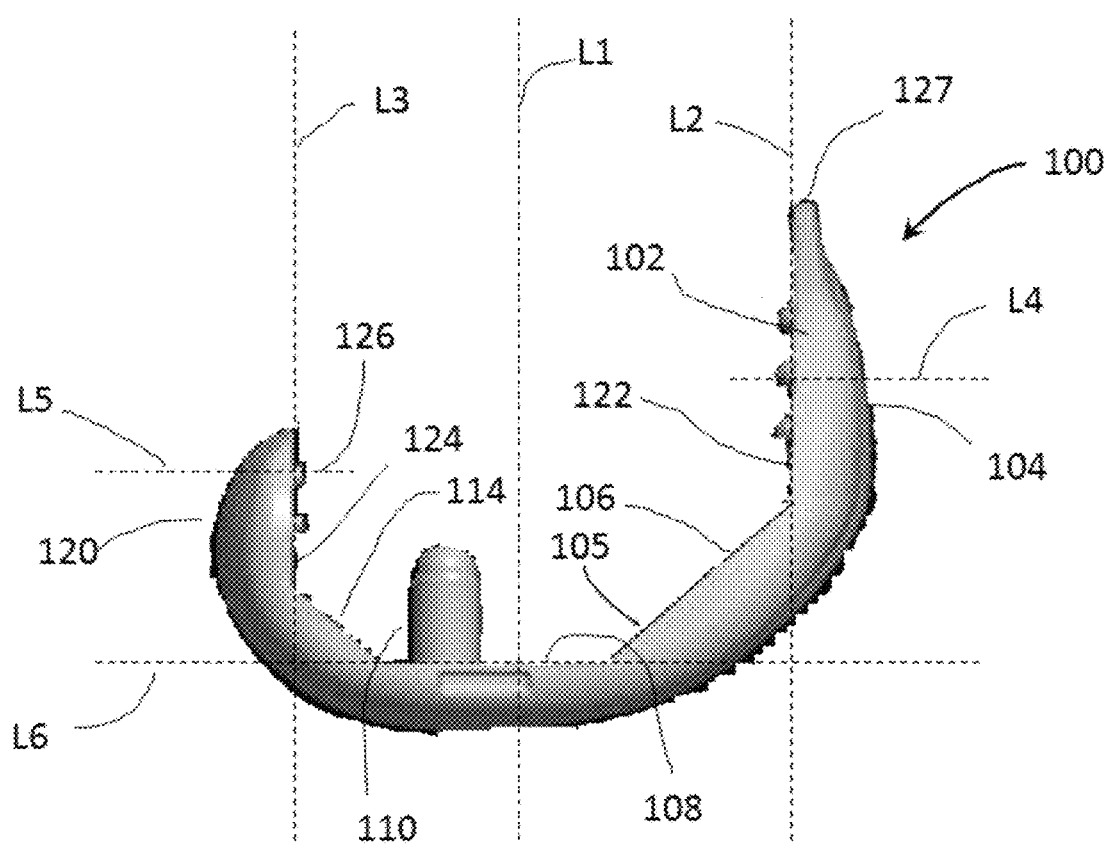
FIG. 2 is a side elevation view of the flexible prosthetic component of FIG. 1.
Figure 3:
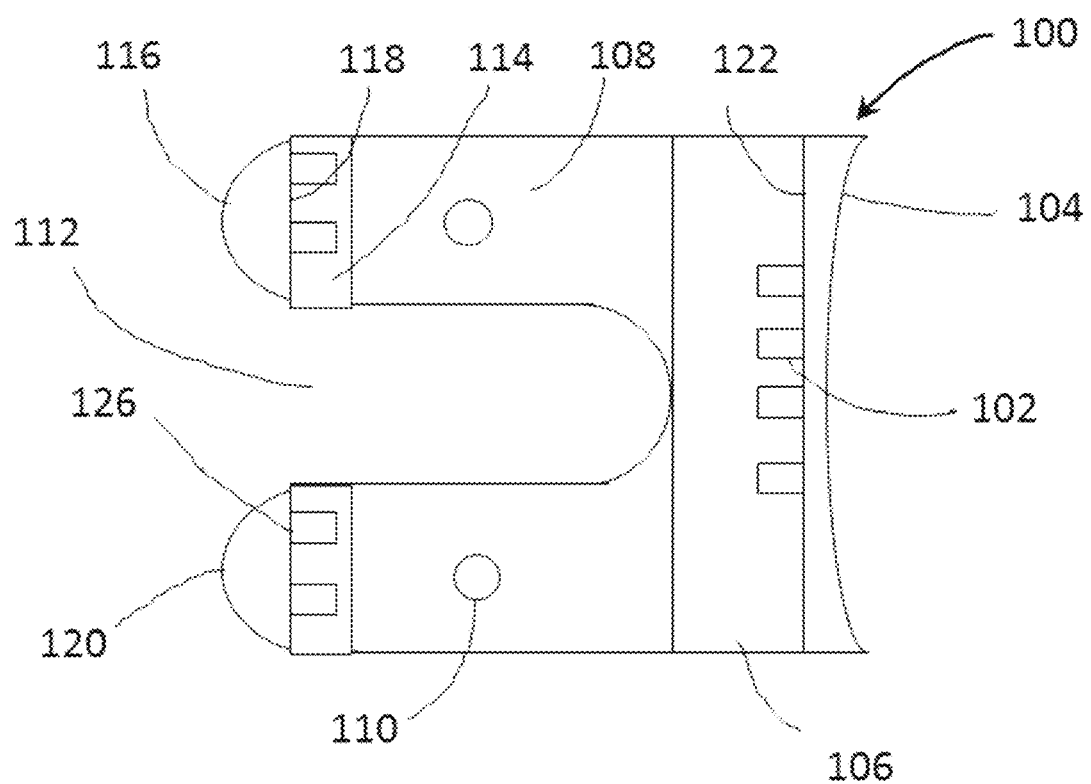
FIG. 3 is a top plan view of the flexible prosthetic component of FIG. 1.

Referring to FIGS. 1-3, there is shown an embodiment of a flexible prosthetic component depicting a distal femoral component 100. Femoral component 100 has an outer articular surface 104 and an opposing inner bone contacting surface 105. Outer articular surface 104 includes an articular condyle surface having a pair of laterally spaced-apart articular posterior condyle surfaces. The outer articular surface is curved to correspond to the convex curvature of a femoral condyle prior to any degeneration or wear thereof. An articular posterior medial condyle surface 116 and an articular posterior lateral condyle surface 120 are separated by a cut-out for the intercondylar notch 112.

The inner bone contacting surface 105 opposing the outer articular surface 104 comprises an anterior surface 122, an anterior chamfer surface 106, a distal surface 108, a posterior chamfer surface 114, a posterior medial condyle surface 118, and a posterior lateral condyle surface 124. A longitudinal axis L1, shown in FIG. 2, is perpendicular to distal surface 108 and parallel to a longitudinal axis L2 of anterior surface 122 and a longitudinal axis L3 of posterior surfaces 114, 118.

Distal surface 108 has two laterally spaced-apart securing posts 110 to aid in the fixation of femoral component 100 to resected bone 10. Protrusions 102 are present on anterior surface 122, and protrusions 126 are present on posterior lateral condyle surface 124 and posterior medial condyle surface 118. These protrusions extend outwardly along axis L4 for the anterior surface and along axis L5 for the posterior lateral condyle surface.

Figure 4:
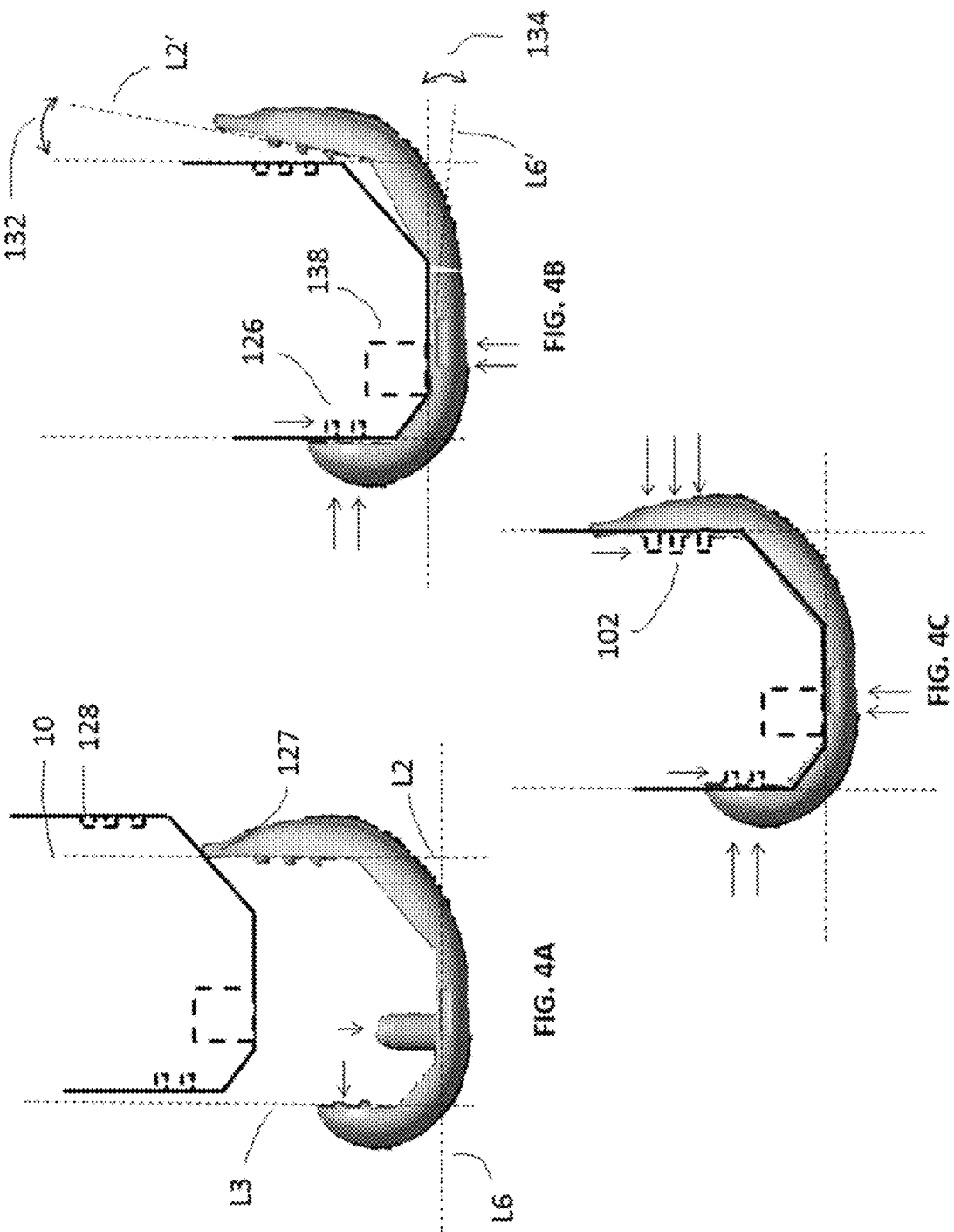
FIGS. 4A-C are side elevation views of the flexible prosthetic component of FIG. 1 showing the sequential steps to secure the flexible prosthetic component to resected bone.

FIGS. 4A-4C show several side elevation views of sequential steps to snap-fit distal femoral component 100 to resected bone 10. FIG. 4A shows a first step in which an apex surface 127 located between articular surface 104 and bone contacting surface 105 contacts an anterior chamfer resected surface on resected bone 10 and is slid in a proximal direction such that at least some of the protrusions on posterior condyle surface 126 and securing posts 110 on the distal surface 108 are at least partially inserted into corresponding recesses or negative engagements 128 and recess 138 cut in resected femur 10. This step secures the posterior lateral condyle surface 124 and distal surface 108 with resected femur 10 by an interference fit.

FIG. 4B shows another step, in which application of an external force by hand or specialized instrument elastically deforms flexible femoral component 100 to snap-fit around resected femur 10. As shown in side elevation view of FIG. 4A, the distance between longitudinal axis L2 and L3 of femoral component 100 in a neutral position about a sagittal plane is less than the corresponding dimension of the resected bone 10. The flexible femoral component 100 must consequently be elastically deformed by the application of an external force to wrap around the resected bone 10. Elastic deformation includes material elongation of femoral component 100 and counterclockwise rotations of longitudinal distal surface axis L6 to meet a longitudinal distal resection axis L6' and axis L2 to L2'. This elastic deformation will align protrusions on anterior surface 102 to engagement features 128 on resected femur, such that these mating parts will snap-fit to anchor distal femoral component 100 to resected bone 10.

FIG. 4C shows the snap-fitted distal femoral component 100 around the resected bone 10. When the external elastic deformation force is removed, compressive forces acting around the distal femoral component 100 will anchor it to the resected bone 10. In addition to the compressive force created by the flexible distal femoral component 100, the interlocking of engagement features on resected bone 10 with protrusions on posterior surface 126 and protrusions on anterior surface 102 will induce stress on the mating parts and result in a stronger bond.

Figure 5:
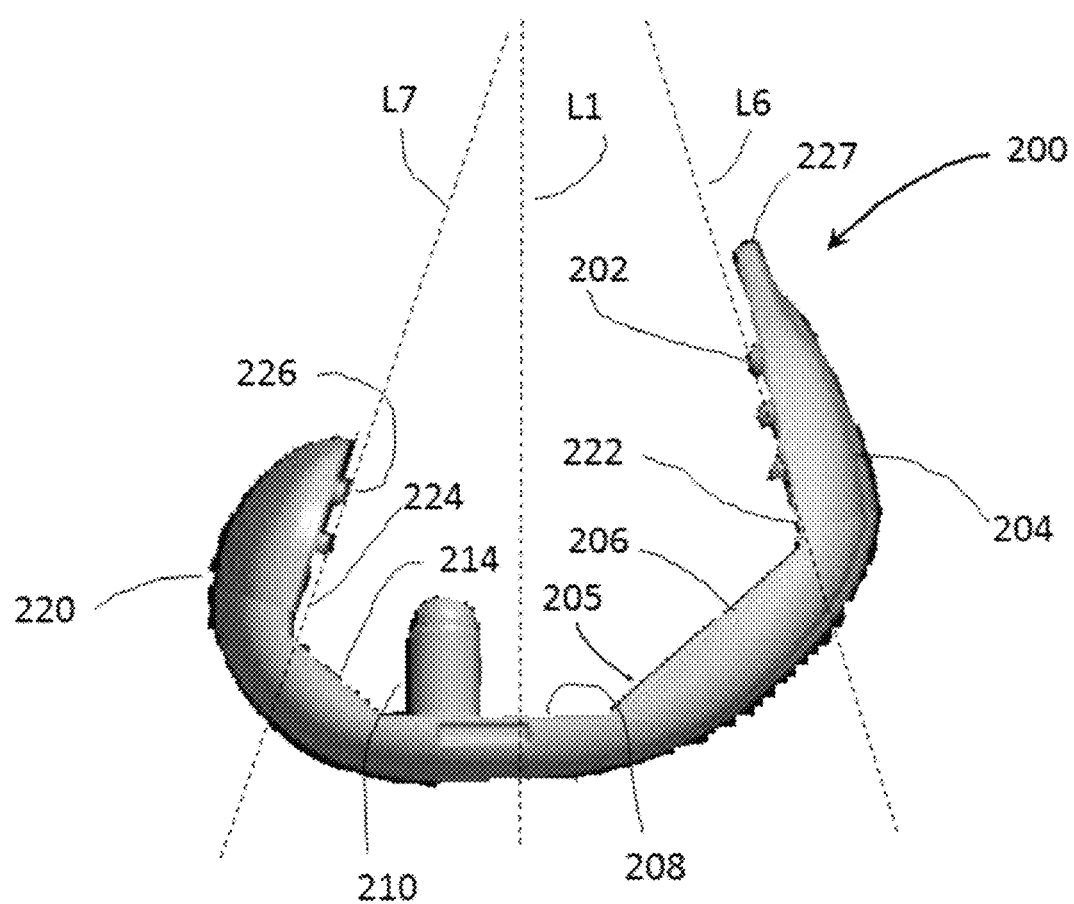
FIG. 5 is a side elevation view of another embodiment of a flexible prosthetic component.

FIG. 5 shows a side elevation of another embodiment of a flexible prosthetic component depicting a distal femoral component 200. Femoral component 200 has an outer articular surface 204 and an opposing inner bone contacting surface 205. Outer articular surface 204 includes an articular condyle surface having a pair of laterally spaced-apart articular posterior condyle surfaces. The outer articular surface is curved to correspond to the convex curvature of the femoral condyle prior to any degeneration or wear thereof. An articular posterior medial condyle surface and an articular posterior lateral condyle surface 220 are separated by a cut-out for the intercondylar notch.

The inner bone contacting surface 205 opposing the outer articular surface 204 comprises an anterior surface 222, an anterior chamfer surface 206, a distal surface 208, a posterior chamfer surface 214, a posterior medial condyle surface, and a posterior lateral condyle surface 224. The inner anterior and posterior surfaces are separated by distal surface 208. Longitudinal axis L1 is perpendicular to distal surface 208.

Distal surface 208 has two laterally spaced-apart securing posts 210 to aid in the fixation of the femoral component 200 to resected bone 10. Protrusions 202 are present on anterior surface 222, and protrusions 226 are present on posterior lateral condyle surface 224 and posterior medial condyle surface.

Anterior surface 222, posterior medial condyle surface, and posterior lateral condyle surfaces 224 are set at acute angles with respect to the distal surface 208. This configuration increases the compressive forces acting on the inner bone contacting surfaces resulting in a tighter bond between the femoral component 200 and the resected bone 10. Procedure to snap-fit femoral component 200 is similar to steps outlined in FIG. 4A-4C.

Figure 6:
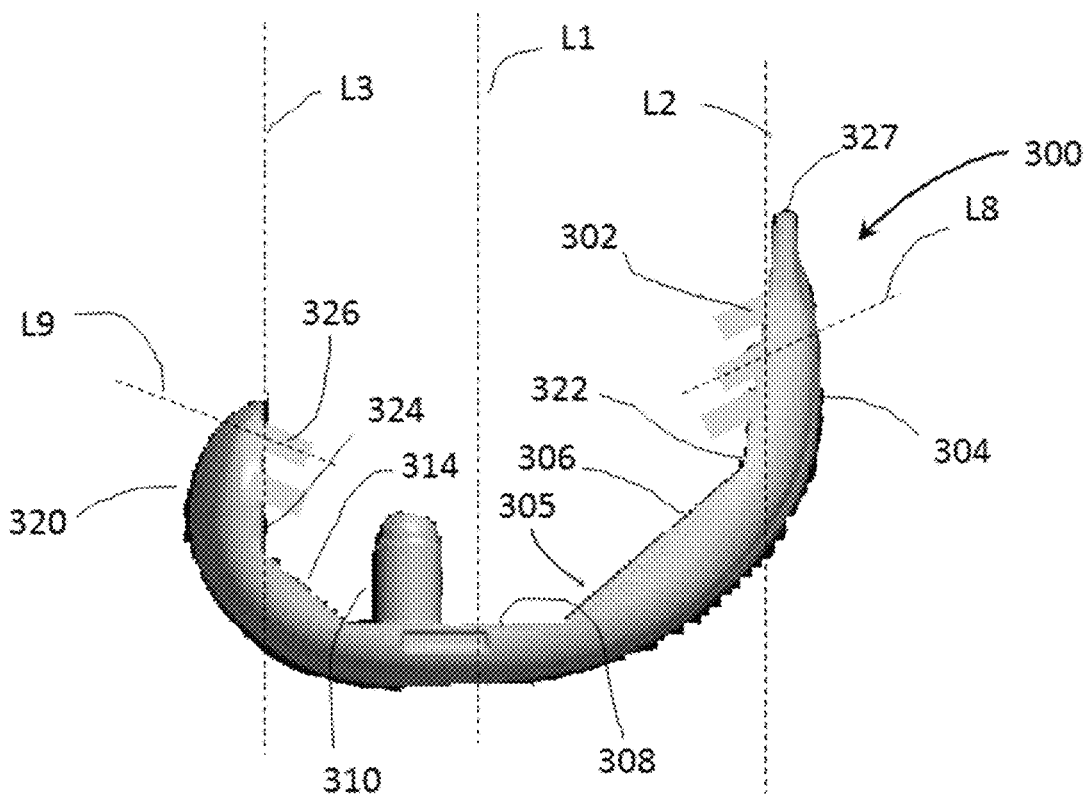
FIG. 6 is a side elevation view of yet another embodiment of a flexible prosthetic component.

FIG. 6 shows a side elevation of a yet another embodiment of a flexible prosthetic component depicting a distal femoral component 300. Femoral component 300 has an outer articular surface 304 and an opposing inner bone contacting surface 305. Outer articular surface 304 includes an articular condyle surface having a pair of laterally spaced-apart articular posterior condyle surfaces. The outer articular surface is curved to correspond to the convex curvature of the femoral condyle prior to any degeneration or wear thereof. An articular posterior medial condyle surface and an articular posterior lateral condyle surface 320 are separated by a cut-out for the intercondylar notch.

The inner bone contacting surface 305 opposing the outer articular surface 304 comprises an anterior surface 322, an anterior chamfer surface 306, a distal surface 308, a posterior chamfer surface 314, a posterior medial condyle surface, and a posterior lateral condyle surface 324. Longitudinal axis L1 is perpendicular to distal surface 308 and parallel to longitudinal axis of anterior surface L2 and longitudinal axis of posterior condyle surface L3.

Distal surface 308 has two laterally spaced-apart securing posts 310 to aid in the fixation of femoral component 300 to resected bone 10. Protrusions 302 are present on anterior surface 322, and protrusions 326 are present on posterior lateral condyle surface 324 and posterior medial condyle surface. Protrusions extend outwardly and inferiorly along axis L8 for the anterior surface and along axis L9 for the posterior lateral condyle surface. When angled protrusions are inserted into matching corresponding recesses in resected bone 10, this mating provides an additional degree of constraint by interlocking prosthesis to bone and thereby negating forces acting directly perpendicular to the anterior or posterior surfaces of femoral component 300. Procedure to snap-fit distal femoral component 300 is similar to steps outlined in FIG. 4A-4C.

Figure 7:
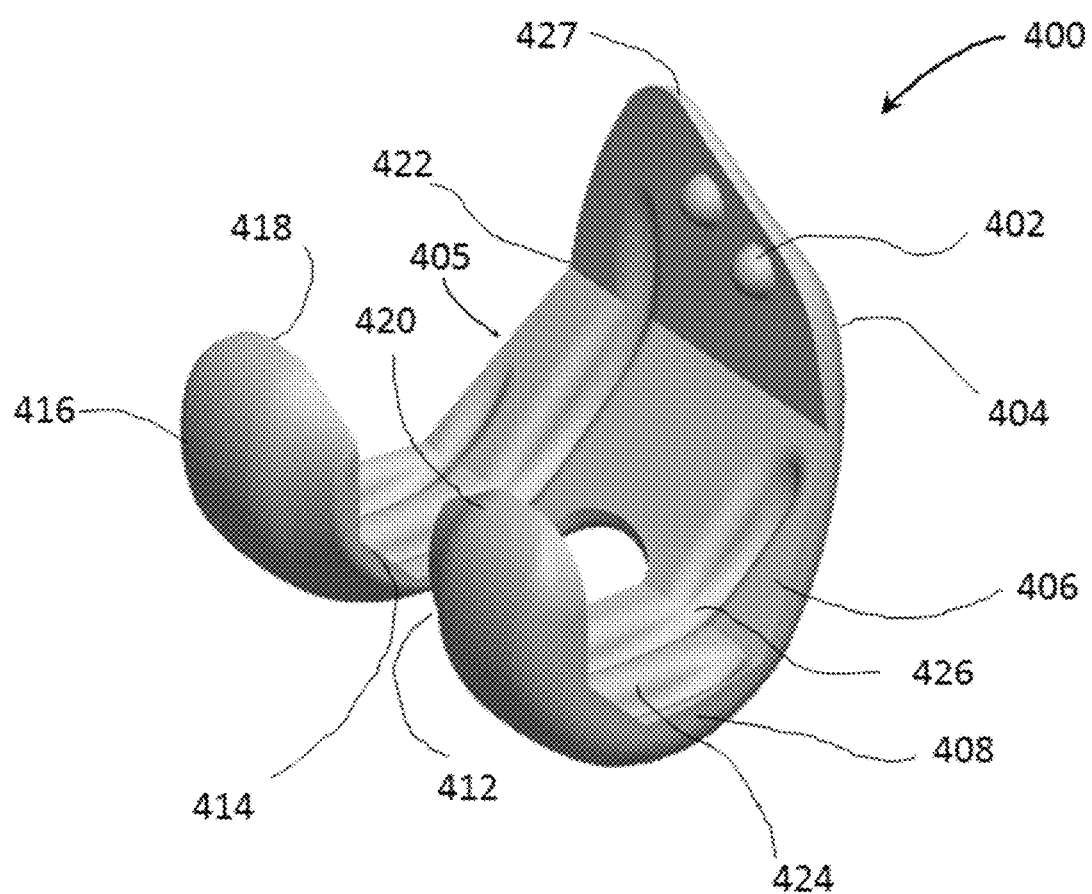
FIG. 7 is a perspective view of a still yet another embodiment of a flexible prosthetic component.
Figure 8:
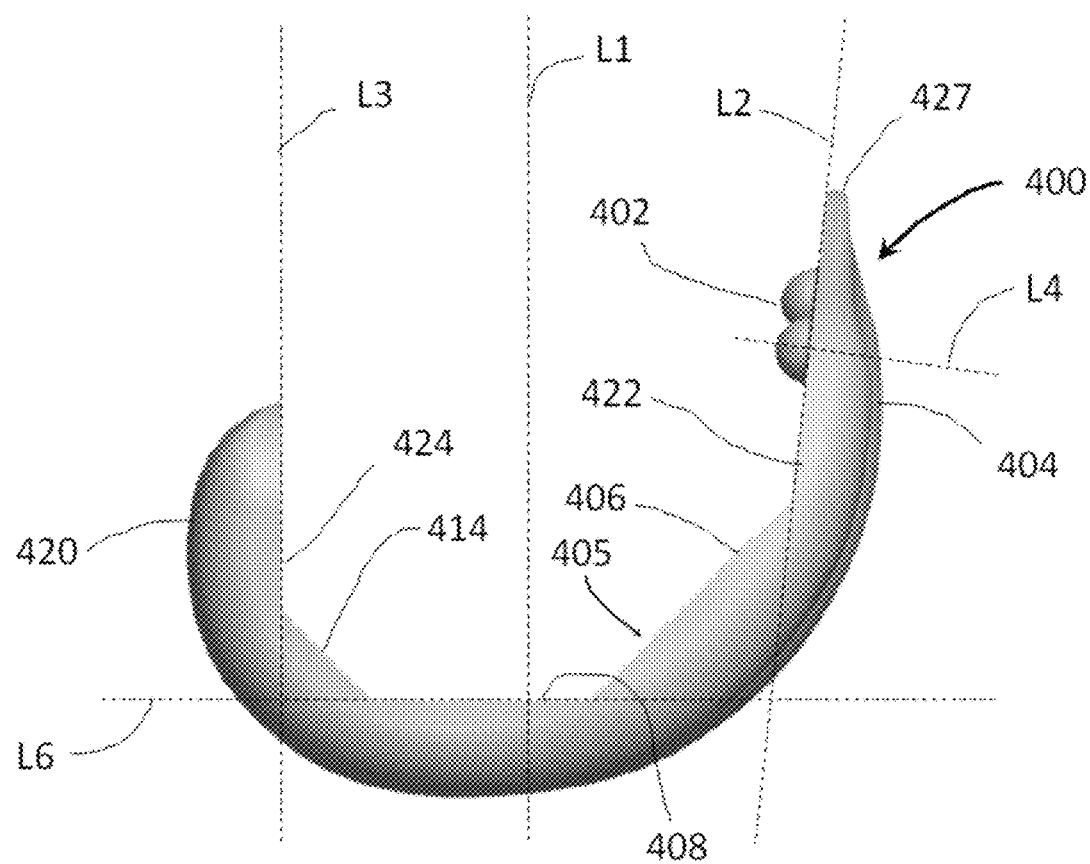
FIG. 8 is side elevation view of the flexible prosthetic component of FIG. 7.

FIGS. 7 and 8 show a still yet another embodiment of a flexible prosthetic component depicting a distal femoral component 400. Femoral component 400 has an outer articular surface 404 and an opposing inner bone contacting surface 405. Outer articular surface 404 includes an articular condyle surface having a pair of laterally spaced-apart articular posterior condyle surfaces. The outer articular surface is curved to correspond to the convex curvature of a femoral condyle prior to any degeneration or wear thereof. An articular posterior medial condyle surface 416 and an articular posterior lateral condyle surface 420 are separated by a cut-out for the intercondylar notch 412.

The inner bone contacting surface 405 opposing the outside articular surface 404 comprises an anterior surface 422, an anterior chamfer surface 406, a distal surface 408, a posterior chamfer surface 414, a posterior medial condyle surface 418, and a posterior lateral condyle surface 424. The inner anterior and posterior surfaces are separated by a distal surface 408. Longitudinal axis L1 is perpendicular to distal surface 408 and parallel to longitudinal axis of the posterior condyle surface L3. Longitudinal axis L2 of the inner anterior surface is set at an obtuse angle to longitudinal axis of distal surface L6.

All five interior prosthetic surfaces have positive 402 and negative features 426 to aid in the fixation of the femoral component 400 to resected bone 10. Protrusions 402 extending outwardly along axis L4 are present on anterior surface 422. Procedure to snap-fit distal femoral component 400 is similar to steps outlined in FIG. 4A-4C. Protrusion and recess features may also include those prepared so as to allow for a rotation about a single pivot point or different pivot points between the prosthetic component and the resected bone as described in U.S. Pat. Pub. No. 2012/0330429, the disclosure of which is hereby incorporated by reference herein.

Figure 9:
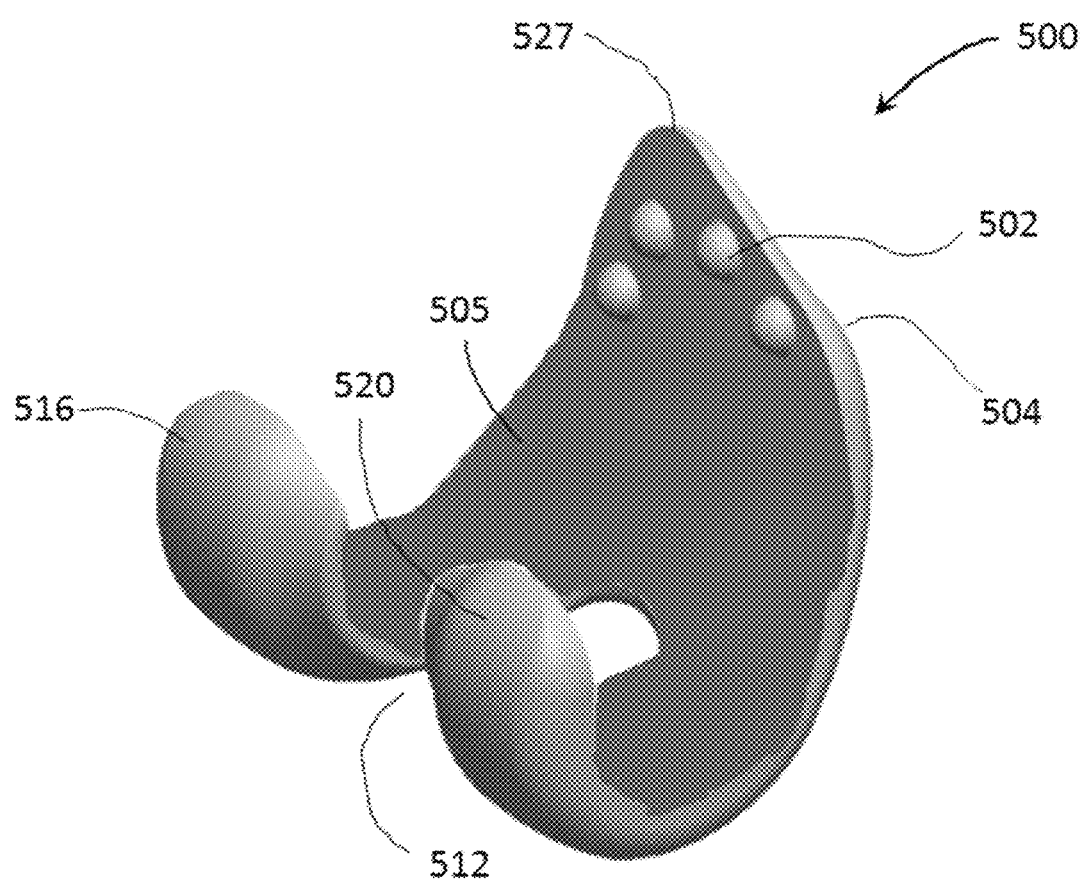
FIG. 9 is a perspective view of a still yet another embodiment of a flexible prosthetic component.
Figure 10:
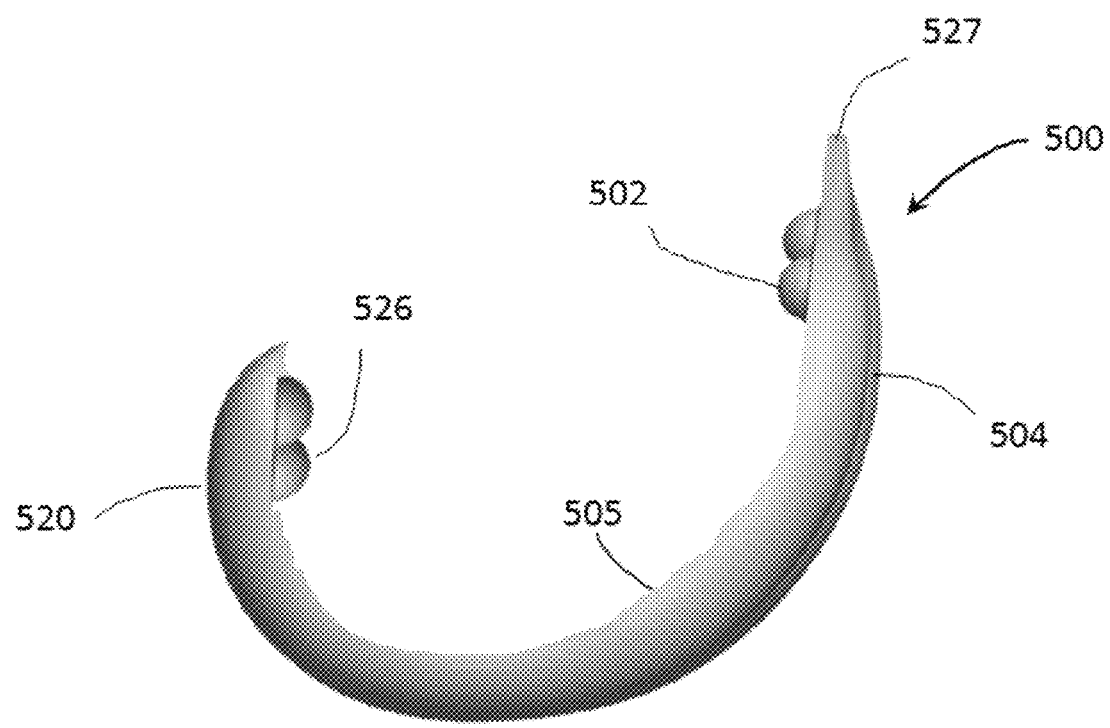
FIG. 10 is a side elevation view of the flexible prosthetic component of FIG. 9.

FIGS. 9 and 10 show another embodiment of a flexible prosthetic component. Distal femoral component 500 has an outer articular surface 504 and an opposing inner bone contacting surface 505. In this embodiment, the inner bone contacting surface 505 is curved to correspond to the convex curvature of an osteoporotic bone or a resurfaced distal femur. Outer articular surface 504 includes an articular condyle surface having a pair of laterally spaced-apart articular posterior condyle surfaces. The outer articular surface is curved to correspond to the convex curvature of the distal femur prior to any degeneration, wear and/or resection thereof. An articular posterior medial condyle surface 516 and an articular posterior lateral condyle surface 520 are separated by a cut-out for the intercondylar notch 512.

The inner curved bone contacting surface 505 has positive features 502, 526 on the respective anterior and posterior surfaces thereof. The distal femoral component 500 is substantially of uniform thickness such separated by the inner bone contacting surface 505 and the outer articular surface 504. Uniform thickness of the distal femoral component 500 allows for minimal bone removal by femoral resurfacing to snap-fit femoral component over resurfaced bone and to repair the articular surface of the distal femur.

Figure 11B:
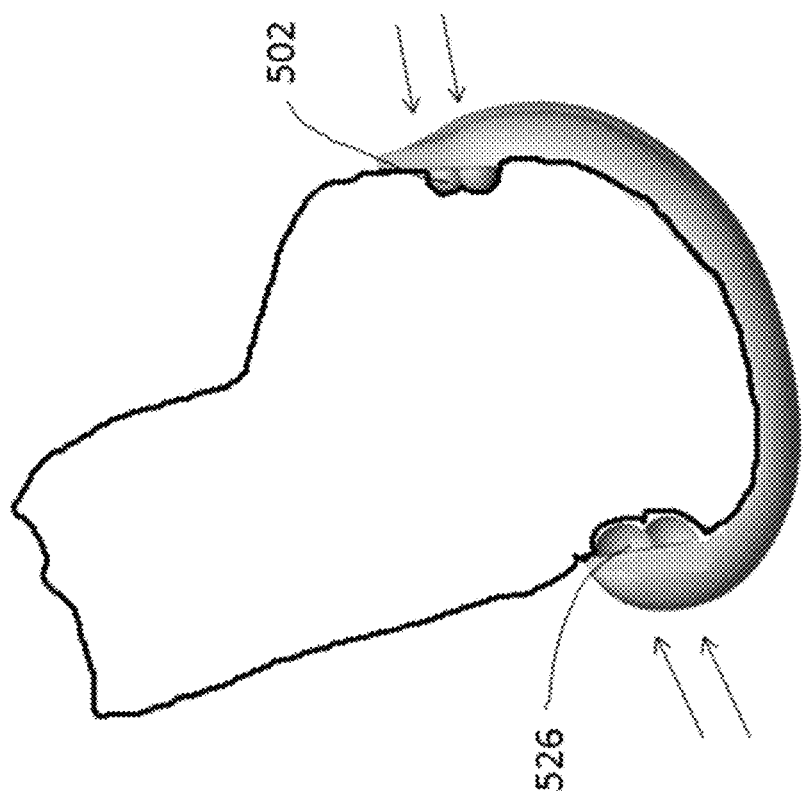
FIGS. 11A and 11B are side elevation views of the flexible prosthetic component of FIG. 9 showing the sequential steps to secure the flexible prosthetic component to resurfaced bone.
Figure 11A:
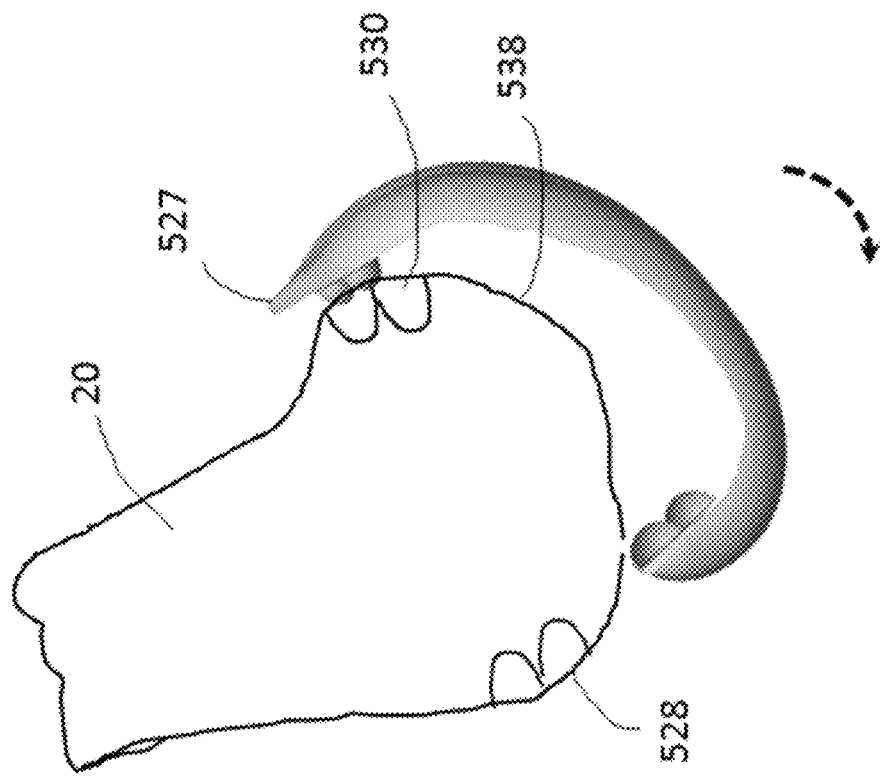

FIGS. 11A and 11B show side elevation views illustrating sequential steps of one method to snap-fit distal femoral component 500 to resurfaced bone 20 having an articular surface 538. Articular surface 538 may be an osteoporotic bone surface being an irregularly shaped convex surface. In some embodiments, inner bone contacting surface 505 may be shaped to conform to articular surface 538 whether it be a native bone surface that has been at least partially degenerated or resurfaced using standard or robotic instrumentation. FIG. 11A shows a first step in which an apex surface 527 located between the outer articular surface 504 and the bone contacting surface 505 of femoral component 500 contacts an anterior surface of the resurfaced bone 20 such that at least some of the protrusions 502 on the anterior surface of the femoral component 500 are at least partially inserted into corresponding recesses or negative engagements 530 in the resurfaced bone 20. This step preferably secures the anterior surface of the femoral component 500 to the anterior surface of the resurfaced bone 20 by an interference fit.

FIG. 11B shows another step, in which application of an external force by hand or specialized instrument elastically deforms the flexible femoral component 500 to snap-fit around the posterior surface of the resurfaced femur 20. The bone contacting inner surface area of the femoral component 500, in a neutral position, is slightly smaller than the recipient resurfaced bone 20. The flexible femoral component 500 must consequently be elastically deformed by sliding and stretching the femoral component by the application of an external force to wrap around the resurfaced bone such that protrusions 526 on the posterior surface of the femoral component 500 snap-fit with the corresponding recesses 528 on the resurfaced bone 20. The femoral component 500 of this embodiment is made of substantially uniform thickness to allow for minimal bone removal during bone resurfacing. In other embodiments, the thickness of a flexible prosthetic may be varied to compensate for femoral degeneration. Bone resections, including resurfacing to implant a flexible femoral component 500 to a resected distal femur may include dynamic trialing methods described in U.S. Pat. Pub. No. 2015/0057758, the disclosure of which is hereby incorporated by reference herein.

Flexible snap-fit prosthetics can be made using suitable biocompatible polymers such as polyetherehterketone ("PEEK"). Thin metal constructs can also be used. Material flexibility, rigidity, and strength are key factors for material selection to achieve functionality and benefits described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A flexible prosthetic component comprising:
   an articular surface; and
   a bone contacting surface opposing the articular surface, the bone contacting surface having an anterior surface and an opposing posterior surface each having one or more protrusions extending outwardly therefrom, wherein the anterior and posterior surfaces are parallel to one another prior to implantation,
   wherein the anterior and posterior surfaces flex toward and away from one another during implantation, such that the one or more protrusions are configured to snap-fit into corresponding recesses made in resected bone, and
   wherein the anterior and posterior surfaces are parallel to one another after implantation.

2. The flexible prosthetic component of claim 1, wherein the anterior and posterior surfaces are separated by at least a distal surface.

3. The flexible prosthetic component of claim 1, wherein said flexible prosthetic component is made of PEEK.

4. The flexible prosthetic component of claim 1, wherein the one or more protrusions on at least one of the posterior and anterior surfaces extend outwardly and inferiorly toward a longitudinal axis of the flexible prosthetic component such that the one or more protrusions may ratchet into the corresponding recesses.

5. A flexible prosthetic component comprising:
   an articular surface; and
   a bone contacting surface opposing the articular surface, the bone contacting surface having an anterior surface and an opposing posterior surface separated by at least a distal surface,
   wherein a longitudinal axis is perpendicular to the distal surface and acute to both the anterior and posterior surfaces prior to implantation,
   wherein each of the anterior and posterior surfaces have one or more protrusions extending outwardly therefrom, the anterior and posterior surfaces being able to flex toward and away from one another during implantation, such that the one or more protrusions are configured to snap-fit into corresponding recesses made in resected bone, and
   wherein the longitudinal axis is perpendicular to the distal surface and acute to both the anterior and posterior surfaces after implantation.

6. The flexible prosthetic component of claim 5, wherein the anterior and posterior surfaces are planar.

7. The flexible prosthetic component of claim 5, wherein an anterior chamfer surface is located between the anterior and distal surfaces.

8. The flexible prosthetic component of claim 7, wherein a posterior chamfer surface is located between the posterior and distal surfaces.

9. The flexible prosthetic component of claim 5, wherein the one or more protrusions on at least one of the posterior and anterior surfaces extend outwardly and inferiorly toward the longitudinal axis such that the one or more protrusions may ratchet into the corresponding recesses.

* * * * *